United States Patent
Avirovikj et al.

(10) Patent No.: US 12,290,334 B2
(45) Date of Patent: May 6, 2025

(54) CONTINUOUS ANALYTE MONITORING DEVICES AND SYSTEMS HAVING A LONG-LIFE REUSABLE WIRELESS TRANSMITTER UNIT AND APPLICATION METHODS THEREFOR

(71) Applicant: Ascensia Diabetes Care Holdings AG, Basel (CH)

(72) Inventors: Dragan Avirovikj, Stamford, CT (US); Jon Taylor, Groton, MA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 363 days.

(21) Appl. No.: 17/704,683

(22) Filed: Mar. 25, 2022

(65) Prior Publication Data
US 2022/0313090 A1    Oct. 6, 2022

Related U.S. Application Data (60) Provisional application No. 63/168,196, filed on Mar. 30, 2021.

(51) Int. Cl.
*A61B 5/00* (2006.01)
*A61B 5/145* (2006.01)

(52) U.S. Cl.
CPC ........ *A61B 5/0031* (2013.01); *A61B 5/14503* (2013.01); *A61B 5/14532* (2013.01);
(Continued)

(58) Field of Classification Search
CPC .............. A61B 5/0031; A61B 5/14503; A61B 5/14532; A61B 2560/0456;
(Continued)

(56) References Cited

U.S. PATENT DOCUMENTS

| | | | |
|---|---|---|---|
| 7,928,850 B2 * | 4/2011 | Hayter | A61B 5/0015 600/347 |
| 8,287,454 B2 * | 10/2012 | Wolpert | A61M 5/1723 600/365 |

(Continued)

FOREIGN PATENT DOCUMENTS

| | | | | |
|---|---|---|---|---|
| AU | 2019313135 A1 | 11/2021 | | |
| WO | WO-2005051170 A2 * | 6/2005 | | A61B 5/076 |

(Continued)

OTHER PUBLICATIONS

International Search Report and Written Opinion issued Jul. 29, 2022 for PCT Patent Application PCT/EP2022/058226.

(Continued)

*Primary Examiner* — Anh Tuan T Nguyen
*Assistant Examiner* — Shankar Raj Ghimire
(74) *Attorney, Agent, or Firm* — Erise IP, P.A.

(57) ABSTRACT

A wearable continuous analyte monitoring (CAM) device includes a disposable sensor unit and a long-life reusable transmitter unit. The transmitter unit has no power source and has an enclosure that seals wireless transmitter circuitry within. The disposable sensor unit is configured to receive and provide power to the transmitter unit therein. Upon expiration of the disposable sensor unit, the transmitter unit can be removed from the disposable sensor unit and reused in another disposable sensor unit with a fresh power source. The CAM device has a cover constructed of a fabric material to improve aesthetics and feel of the CAM device. Methods of preparing and applying the CAM device to a user's skin are also provided, as are other aspects.

22 Claims, 6 Drawing Sheets

(52) U.S. Cl.
CPC . *A61B 2560/0456* (2013.01); *A61B 2560/063* (2013.01); *A61B 2562/164* (2013.01); *A61B 2562/227* (2013.01)

(58) Field of Classification Search
CPC ........ A61B 2560/063; A61B 2562/164; A61B 2562/227
See application file for complete search history.

(56) References Cited

U.S. PATENT DOCUMENTS

| | | | |
|---|---|---|---|
| 8,333,714 B2* | 12/2012 | Stafford | G16H 10/60 600/347 |
| 8,456,301 B2* | 6/2013 | Fennell | A61B 5/1473 600/347 |
| 9,795,326 B2* | 10/2017 | Hoss | A61B 5/14865 |
| 11,911,174 B2* | 2/2024 | Dunn | A61B 5/7275 |
| 11,943,876 B2* | 3/2024 | Halac | G01N 33/66 |
| 2008/0161656 A1 | 6/2008 | Bruce et al. | |
| 2008/0242962 A1 | 10/2008 | Roesicke et al. | |
| 2014/0163338 A1 | 6/2014 | Roesicke | |
| 2014/0316223 A1* | 10/2014 | Heck | A61B 46/10 206/703 |
| 2017/0091259 A1* | 3/2017 | Curran | G06F 16/2343 |
| 2017/0112533 A1 | 4/2017 | Schoonmaker et al. | |
| 2017/0112534 A1* | 4/2017 | Schoonmaker | A61B 17/3468 |
| 2017/0173262 A1* | 6/2017 | Veltz | G16H 20/17 |
| 2017/0188912 A1* | 7/2017 | Halac | A61B 5/14546 |
| 2017/0238789 A1* | 8/2017 | Iizuka | A61B 1/018 |
| 2017/0290546 A1 | 10/2017 | Antonio et al. | |
| 2018/0153451 A1 | 6/2018 | Heikenfeld et al. | |
| 2019/0046038 A1* | 2/2019 | Weinstein | A61B 5/0024 |
| 2019/0336054 A1 | 11/2019 | Shah et al. | |
| 2019/0336055 A1* | 11/2019 | Shah | H04W 52/02 |
| 2020/0178899 A1 | 6/2020 | Chae et al. | |
| 2021/0212603 A1* | 7/2021 | Gudibande | A61B 5/24 |
| 2021/0228115 A1 | 7/2021 | Prais et al. | |
| 2022/0133183 A1* | 5/2022 | Garai | A61B 5/6833 600/365 |

FOREIGN PATENT DOCUMENTS

| | | | |
|---|---|---|---|
| WO | 2018222010 A1 | 12/2018 | |
| WO | WO-2020027422 A1 * | 2/2020 | ........ A61B 5/0024 |
| WO | 2020221331 A1 | 11/2020 | |
| WO | 2021/148591 A1 | 7/2021 | |
| WO | 2021/148596 A1 | 7/2021 | |
| WO | 2022/207618 A2 | 10/2022 | |

OTHER PUBLICATIONS

International Search Report and Written Opinion issued Nov. 8, 2022 for PCT Patent Application PCT/EP2022/058226.
European Patent Application 22719252.3 Examination Report issued Jan. 24, 2025.

* cited by examiner

CONTINUOUS ANALYTE MONITORING DEVICES AND SYSTEMS HAVING A LONG-LIFE REUSABLE WIRELESS TRANSMITTER UNIT AND APPLICATION METHODS THEREFOR

CROSS REFERENCE TO RELATED APPLICATION

This application claims priority to, and the benefit of, U.S. Provisional Patent Application No. 63/168,196, filed Mar. 30, 2021, the disclosure of which is hereby incorporated by reference in its entirety for all purposes.

FIELD

This disclosure relates to analyte monitoring devices, systems, and application methods therefor.

BACKGROUND

Continuous analyte monitoring (CAM), such as continuous glucose monitoring (CGM), has become a routine monitoring operation, particularly for individuals with diabetes. By providing real-time analyte (e.g., glucose) readings, therapeutic actions may be taken in a more timely fashion and, in the case of a CGM, a glycemic condition may possibly be better controlled. A sensor of a CAM device is typically inserted subcutaneously into a user, while the CAM device adheres to an outer surface of the user's skin, such as on the abdomen or back of the upper arm. The CAM device can be continuously operated such that the sensor provides periodic signals to a wireless transmitter of the CAM device. The signals are indicative of the user's analyte (e.g., glucose) level. A handheld CAM receiver (e.g., a smartphone or other suitable receiver) may process the signals received from the CAM device and display analyte readings. Analyte readings may be provided automatically many times throughout the day (e.g., every few minutes or at some other pre-established time interval).

A CAM device may be worn on the body for several days or even several weeks before removal and replacement of the sensor is required. CAM devices may be disposable or reusable. A disposable CAM device should be removed from a user upon expiration of the sensor and replaced with a new CAM device. A reusable CAM device typically has a replaceable sensor unit connected to a separate wireless transmitter unit that typically has a nonreplaceable rechargeable battery. Upon expiration of the sensor, a reusable CAM device should be removed from a user, the sensor unit should then be replaced with a new sensor unit, and the transmitter unit battery should be recharged. Eventually (e.g., after about 90 days), the rechargeable battery will no longer be usable, thus requiring the entire reusable CAM device to be replaced.

Improved reusable CAM devices are accordingly desired.

SUMMARY

In some embodiments, a wearable continuous analyte monitoring (CAM) device is provided that includes a transmitter unit comprising an enclosure and wireless transmitter circuitry completely sealed within the enclosure. The wireless transmitter circuitry is operative to receive and wirelessly transmit electrical signals indicative of an analyte level. The transmitter unit has no power source therein and has electrical contacts on the enclosure for receiving power and the electrical signals. The CAM device also includes a sensor unit comprising a power source and a sensor. The sensor extends through the sensor unit and is configured to be inserted into skin of a user. The sensor unit has a closable opening for receiving the transmitter unit there through. The sensor unit is configured to generate the electrical signals indicative of an analyte level. The sensor unit is also configured to electrically connect to the electrical contacts of the transmitter unit in response to receiving the transmitter unit through the closable opening. The sensor unit is disposable, and the transmitter unit is removable from the sensor unit through the closable opening and is reusable in another sensor unit. CAM device includes a CAM cover comprising fabric covering the sensor unit.

In some embodiments, a method of preparing and applying a continuous analyte monitoring (CAM) device to a user's skin is provided. The method includes inserting a transmitter unit through an opening in a sensor unit of the CAM device, which is pre-loaded into an applicator. The sensor unit has a sensor extending from the sensor unit and the CAM device. The method also includes closing the opening and attaching a rigid skirt to the applicator. The rigid skirt has a lid attached thereto. The method further includes removing the lid, positioning the applicator on a surface of the user's skin, and actuating the applicator to insert the sensor into the user's skin.

Still other aspects, features, and advantages of this disclosure may be readily apparent from the following detailed description and illustration of a number of example embodiments and implementations, including the best mode contemplated for carrying out the invention. This disclosure may also be capable of other and different embodiments, and its several details may be modified in various respects, all without departing from the scope of the disclosure. For example, although the description below relates to CAM and CGM devices, the non-powered long-life reusable transmitter unit may be readily adapted to other electronic devices that include a disposable component and a reusable component. This disclosure is intended to cover all modifications, equivalents, and alternatives falling within the scope of the claims.

BRIEF DESCRIPTION OF DRAWINGS

The drawings, described below, are for illustrative purposes, and are not necessarily drawn to scale. Accordingly, the drawings and descriptions are to be regarded as illustrative in nature, and not as restrictive. The drawings are not intended to limit the scope of the disclosure in any way.

DETAILED DESCRIPTION

Embodiments described herein provide a continuous analyte monitoring (CAM) device that includes a disposable sensor unit configured to receive and provide power to a long-life, reusable, wireless transmitter unit. The transmitter unit includes an enclosure that completely seals wireless transmitter circuitry and any other components therein, thus protecting the transmitter unit from environmental corrosion, exposure, and other factors. The transmitter unit does not include a power source (e.g., a rechargeable battery, which is typically usable only for a limited time, such as e.g., about 90 days in some known devices). By providing a power source in the disposable sensor unit that also powers the transmitter unit, a user advantageously avoids having to recharge a transmitter unit battery each time a disposable sensor unit is replaced (and thus no longer needs to have a corresponding battery recharger and thus avoids possible fire or other hazards associated with battery recharging). A user also advantageously receives a fresh battery with each new disposable sensor unit, and thus avoids the risk of a power loss by a transmitter unit battery that (often unexpectedly) no longer holds a sufficient charge to power the transmitter unit. Transmitter units according to embodiments described herein may thus be reusable for extended periods of time (e.g., years instead of months).

CAM devices according to embodiments described herein may also include a cover advantageously constructed with a fabric material to improve aesthetics, discreetness, and/or user feel of the CAM device. The look of the CAM device may be customizable by providing different fabrics and/or colors. In particular, the fabric and color may be selected to mimic the look of an adhesive bandage. A web conversion process may be used to produce fabric material covers, which may reduce manufacturing costs as compared to producing conventional CAM device covers.

In accordance with one or more embodiments, CAM devices having disposable sensor units configured to receive and power long-life reusable wireless transmitter units are provided herein. Further, CAM devices comprising fabric covers may be provided herein. CAM devices, systems, and application methods of the present disclosure will be explained in greater detail below in connection with FIGS. 1-8 herein.

Figure 1:
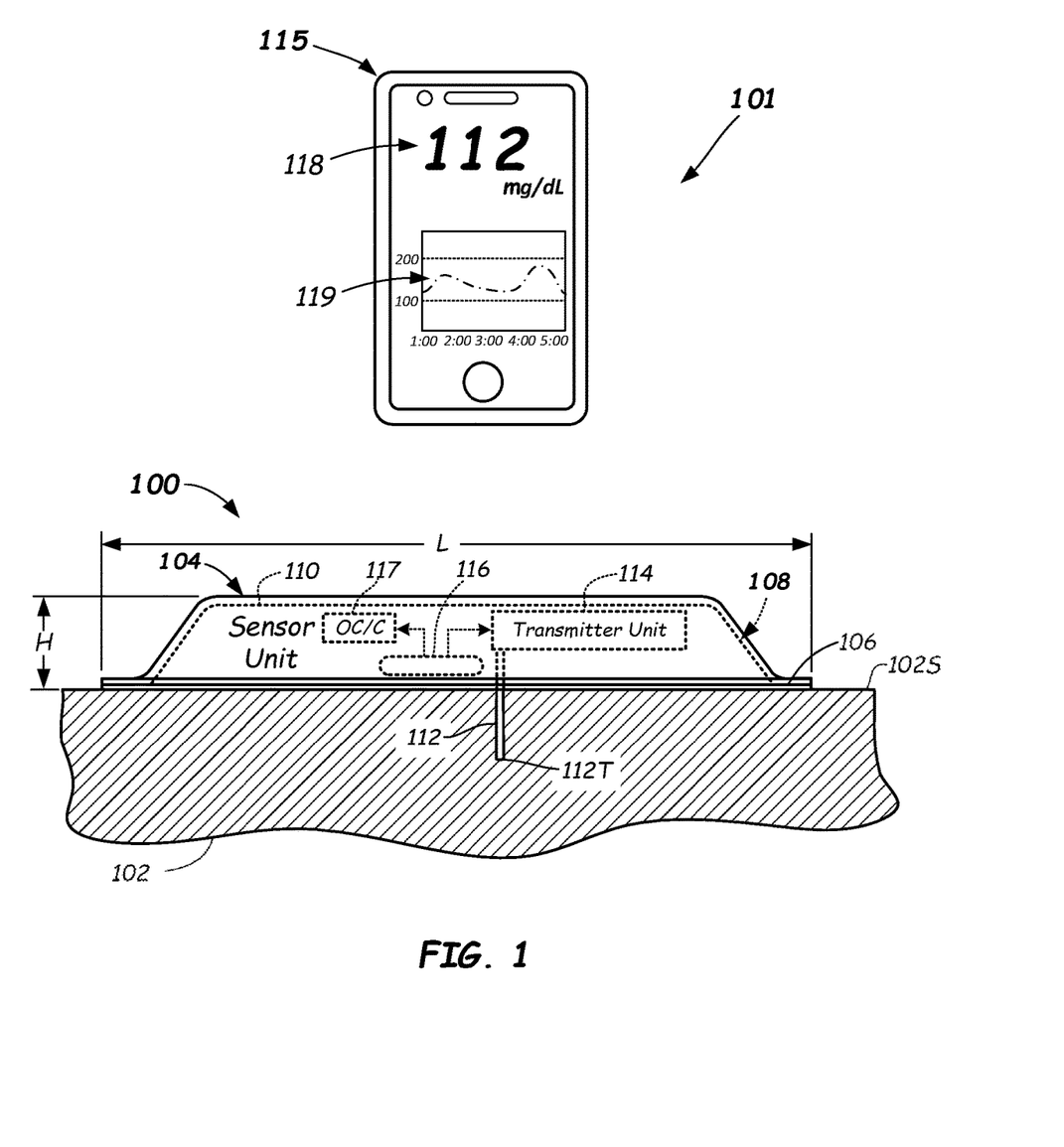
FIG. 1 illustrates a side elevation view of a continuous glucose monitoring (CGM) device that includes a sensor unit and a transmitter unit received within the sensor unit according to embodiments provided herein.

FIG. 1 illustrates a wearable continuous glucose monitoring (CGM) device 100, which is one example of a CAM device, useable as part of an analyte (e.g., glucose) measurement system 101 according to one or more embodiments. As shown, CGM device 100 may be attached (via an adhesive) to a skin surface 102S of a user (shown in partial cross section). CGM devices and methods typically generate electrochemical analyte (e.g., glucose) signals continuously during operation and perform analyte (e.g., glucose) measurements/estimations based on periodically generated signals (e.g., typically every few minutes). That is, CGM device 100 is configured to continuously monitor and provide periodic glucose readings (e.g., every few minutes or other suitable time interval) to one or more external devices 115 of the analyte (e.g., glucose) measurement system 101.

CGM device 100 may include a cover 104 and an adhesive assembly 106 that together may enclose and seal therein a disposable sensor unit 108 therein. Cover 104 may be manufactured from a soft fabric material, and may have a soft and bendable consistency such that it may conform to the contours of the user's skin 102. Cover 104 may be flexible to allow user movement with limited resistance, much like when wearing an adhesive bandage. In particular, cover 104 may be manufactured from a thin flexible woven fabric. Sensor unit 108 may also include a flexible housing 110 wherein adhesive assembly 106 may form a bottom surface thereof (i.e., the surface that engages and attaches to skin surface 102S).

Flexible housing 110 and adhesive assembly 106 form a sensor unit enclosure 110 that is removable from the cover 104. Cover 104 may cover and may be, e.g., form-fitted over the flexible housing 110 in some embodiments. Sensor unit 108 may also include a sensor 112 protruding from a bottom end thereof, a portion of which is shown inserted through the user's skin 102. Sensor 112 may extend from sensor unit 108 and CGM device 100 through adhesive assembly 106 and may be configured to be at least partially located in interstitial fluid in a subcutaneous region of a user. Sensor 112 may be or may include an analyte sensor or an analyte sensor portion, such as at or near a sensor tip 112T. Sensor 112 may generate a measureable current when measuring the analyte (e.g., glucose) of interest. Sensor 112 may be inserted with an applicator (i.e., an insertion device 600 as shown in FIGS. 6A-6E for example) having a sharpened needle or "introducer" that pierces the skin 102 to introduce the sensor 112 into a subcutaneous region of a user.

Sensor unit 108 may also include a removable transmitter unit 114 and a power source 116. Power source 116 provides power to transmitter unit 114 and sensor 112 and, in some embodiments, other sensor circuitry/components (OC/C 117) that may be included in sensor unit 108. Transmitter unit 114 may include wireless transmitter circuitry and/or other electronic components that communicate with sensor 112 and/or other sensor circuitry/components 117 to receive electrical signals indicative of analyte (e.g., glucose) levels. Transmitter unit 114 may also wirelessly communicate with one or more external devices 115 (e.g., a hand-held CGM receiver or other portable device, such as a smartphone or watch executing a suitable CGM application software program) to provide glucose measurement signals and/or glucose measurement results. Such one or more external devices 115 may display analyte readings 118 and/or plotted analyte data 119 illustrating one or more trends. Other information can be displayed, as well. Although the depicted example is glucose, other analytes could be measured, such as lactose or cholesterol provided a suitably selective sensor for those analytes is used.

Figure 2:
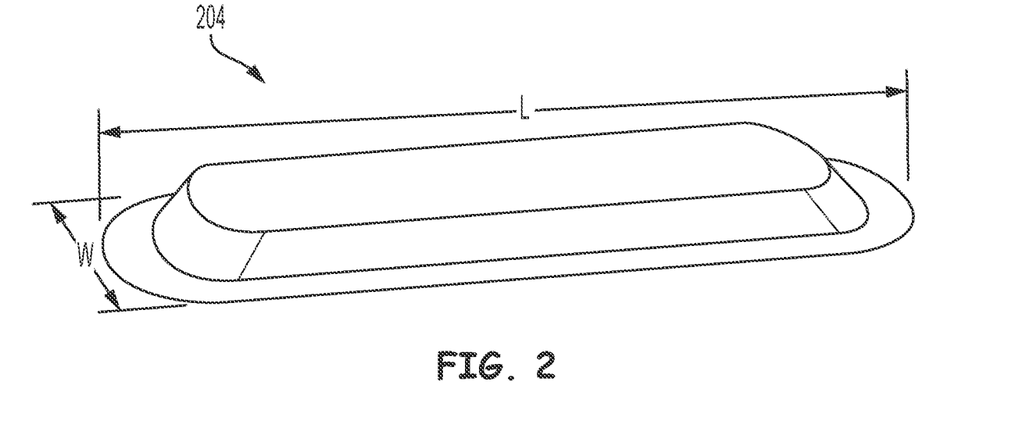
FIG. 2 illustrates a perspective view of a continuous analyte monitoring (CAM) device cover according to embodiments provided herein.

FIG. 2 illustrates an example of a CAM device cover, such as, e.g., cover 104 of FIG. 1, according to one or more embodiments. CAM cover 204 may be constructed with any suitable soft, woven fabric material and may be available in various colors. In some embodiments, CAM cover 204 may be configured to be form-fitted over a sensor unit housing, such as, e.g., flexible housing 110. In other embodiments, CAM cover 204 may be removably attached in any suitable manner to a sensor unit, such as, e.g., sensor unit 108. CAM cover 204 improves aesthetics, discreetness, and/or user feel of a CAM device 100 attached to a user, especially as compared to known CAM devices with hard, rigid covers. CAM cover 204 can have a low profile as compared to its length L. For example, the low profile of the CAM cover and thus the CAM device 100, given the thickness of adhesive assembly 106 is negligible) can be exhibited as having a structure wherein a length to height ratio (L/H ratio) is greater than 4, greater than 6, or even greater than 8 in some embodiments.

Figure 3:
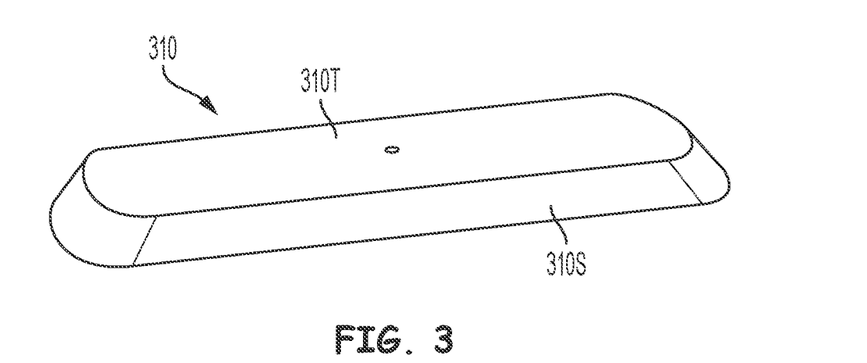
FIG. 3 illustrates a perspective view of a flexible housing of a sensor unit of a CAM device according to embodiments provided herein.

FIG. 3 illustrates an example of a sensor unit housing, such as, e.g., flexible housing 110 of FIG. 1, according to one or more embodiments. Sensor unit housing 310 may include a top 310T and four sides 310S wherein, in some embodiments, an adhesive assembly (such as, e.g., adhesive assembly 106) may form a bottom surface (i.e., the surface applied against a user's skin; the bottom surface not shown in FIG. 3). That is, sensor unit housing 310 and an adhesive assembly 106 may form an enclosure. Sensor unit housing 310 may be constructed with any suitable flexible material that allows sensor unit housing 310 to flex in conformance with contours of a user's skin surface as the user moves about.

Figure 4:
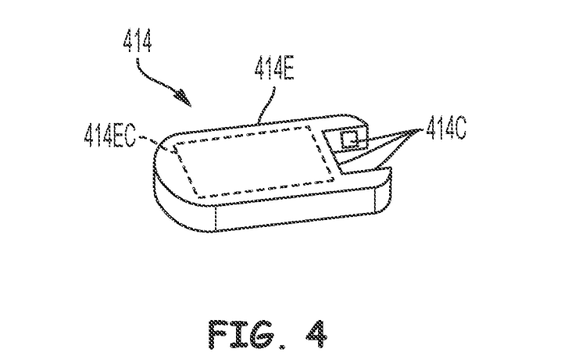
FIG. 4 illustrates a perspective view of a reusable transmitter unit configured to be received in a sensor unit of a CAM device according to embodiments provided herein.

FIG. 4 illustrates an example of a long-life reusable wireless transmitter unit, such as, e.g., transmitter unit 114 of FIG. 1, according to one or more embodiments. Transmitter unit 414 is configured to be received in a sensor unit, such as, e.g., sensor unit 108 of FIG. 1. Transmitter unit 414 may include an enclosure 414E and wireless transmitter circuitry 414EC (shown dotted) that can be completely sealed within enclosure 414E, thus protecting the wireless transmitter circuitry 414CE from environmental factors. The wireless transmitter circuitry 414CE is operative to receive and wirelessly transmit electrical signals indicative of an analyte level to one or more external devices 115 via any suitable wireless protocol and radio. Transmitter unit 414 has no power source therein. Transmitter unit 414 may include one or more electrical contacts 414C accessible on one or more external surfaces of enclosure 414E for receiving power and the electrical signals indicative of the analyte level. Transmitter unit 414 may have other shapes and/or configurations than the one shown in FIG. 4 and FIG. 8 herein.

Figure 5:
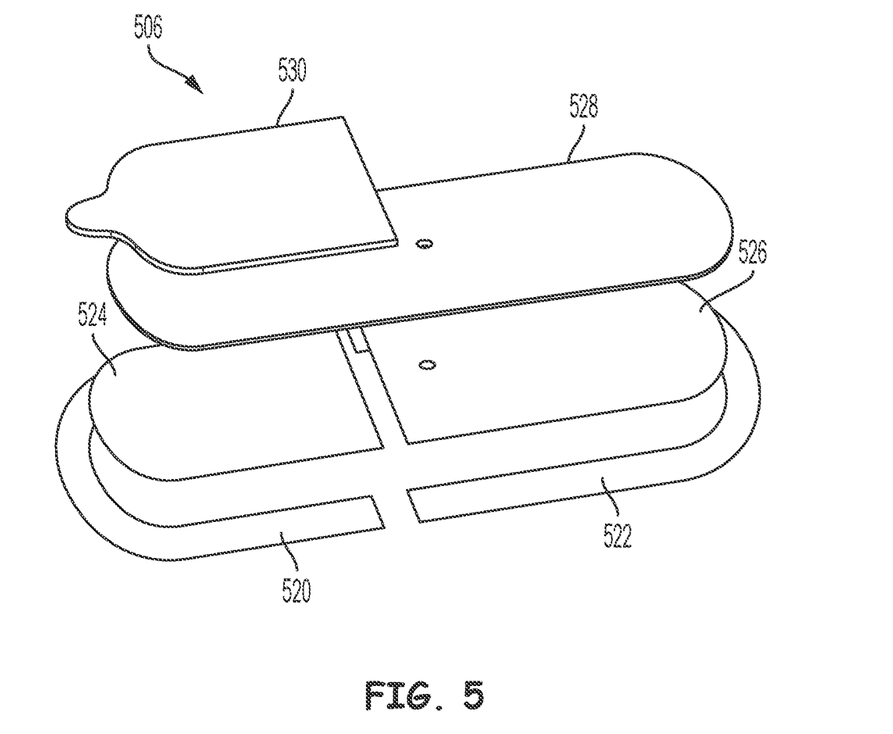
FIG. 5 illustrates an exploded perspective view of an adhesive assembly of a CAM device according to embodiments provided herein.

FIG. 5 illustrates an example of the individual parts of an adhesive assembly, such as, e.g., adhesive assembly 106 of FIG. 1, according to one or more embodiments. Adhesive assembly 506 may be used in some embodiments to form a bottom surface of a sensor unit and/or (concurrently) a CAM device. A "bottom surface" is defined herein as a surface that will be in contact with a user's skin upon attachment of the CAM device to the skin surface 102S of the user's skin 102. Adhesive assembly 506 may include a first perimeter segment 520, a second perimeter segment 522, a hinged adhesive flap 524, an adhesive main section 526, a removable adhesive backer 528, and a removable adhesive flap backer 530. Hinged adhesive flap 524 and adhesive main section 526 both have a same side having an adhesive thereon suitable for attaching to the skin surface 102S of a user's skin 102. Removable adhesive backer 528 may be sized to cover and protect the adhesive side of hinged adhesive flap 524 and adhesive main section 526 until a CAM device is ready to be applied to the skin surface 102S of the user's skin 102. Hinged adhesive flap 524 may also have a second side having an adhesive thereon, and removable adhesive flap backer 530 is sized to cover and protect that second side also until a CAM device is ready to be applied to a user's skin, as described in more detail below in connection with FIGS. 6A-6F.

In some embodiments, first perimeter segment 520 and second perimeter segment 522 may not have any side with an adhesive thereon, while in other embodiments, first perimeter segment 520 and second perimeter segment 522 may have an adhesive suitable for attaching to a skin surface 102S of the user's skin on a same side thereof as hinged adhesive flap 524 and adhesive main section 526. In those embodiments, removable adhesive backer 528 may be sized to also cover and protect first perimeter segment 520 and second perimeter segment 522. Any suitable adhesive material (e.g., any suitable single or double-sided adhesive tape or pressure sensitive adhesive) and any suitable adhesive backer material may be used for one or more of first perimeter segment 520, second perimeter segment 522, hinged adhesive flap 524, adhesive main section 526, removable adhesive backer 528, and removable adhesive flap backer 530. Other configurations of adhesive assembly 506 may be possible.

Figure 6A:
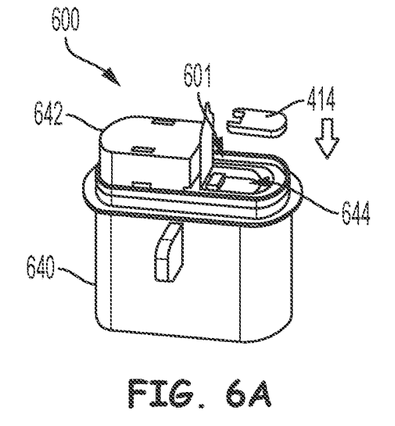
FIGS. 6A, 6B, 6C, 6D, 6E, and 6F illustrate perspective views of steps to be performed for preparing and applying a CAM device to a user's skin according to embodiments provided herein.

FIGS. 6A, 6B, 6C, 6D, 6E, and 6F illustrate a method including various configuration stages to be performed for preparing and applying a CAM device to a user's skin 102 according to one or more embodiments. FIG. 6A shows an applicator 600 having a CAM device 601 pre-loaded in a main body 640 of the applicator 600. CAM device 601 may be, e.g., CGM device 100 of FIG. 1. (Note that CAM device 601 is shown in FIGS. 6A-6D positioned in main body 640 upside down from that shown in FIG. 1 for CGM device 100.) Applicator 600 also includes a safety cover 642 positioned over a sensor (not shown) extending out from a bottom of a sensor unit of CAM device 601. Long-life reusable wireless transmitter unit 414 may be inserted through a closable opening 644 of the sensor unit of the CAM device 601.

Figure 6B:
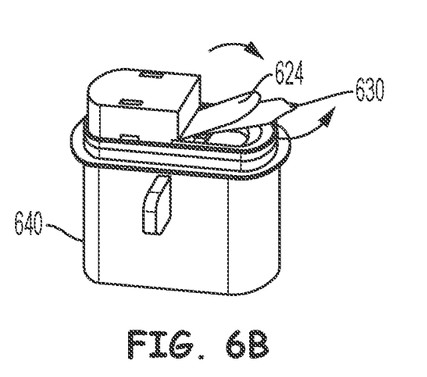

As shown in FIG. 6B, after transmitter unit 414 is inserted into the sensor unit, a removable adhesive flap backer 630 (which may be similar or identical to removable adhesive flap backer 530 of FIG. 5) may be removed from a hinged adhesive flap 624 (which may be similar or identical to hinged adhesive flap 524 of FIG. 5). After removal of adhesive flap backer 630, hinged adhesive flap 624 may be sealed over transmitter unit 414. This can hermetically seal the transmitter unit 414 in the closable opening 644.

Figure 6C:
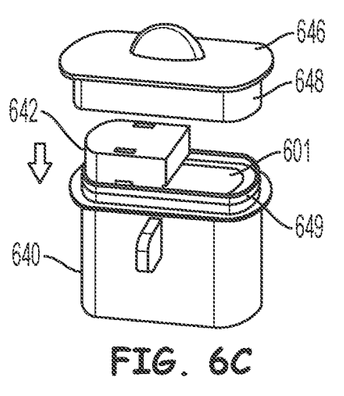

In FIG. 6C, an assembly of a lid 646 and a rigid skirt 648 may be mounted onto main body 640 over safety cover 642 and CAM device 601. Upon mounting onto main body 640, lid 646 engages and attaches to safety cover 642, while rigid skirt 648 engages and attaches to main body 640 (e.g., via, e.g., a snap-on action over a corresponding ridge 649 along some or all of the perimeter of the top of main body 640).

Figure 6D:
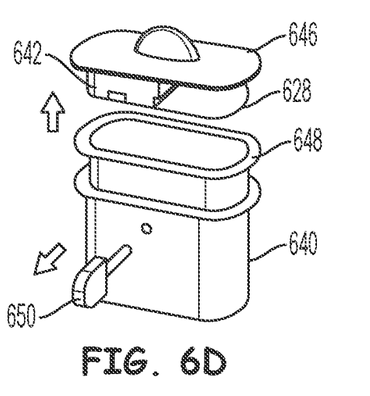

FIG. 6D shows lid 646 being removed from main body 640, wherein safety cover 642 and a removable adhesive backer 628 (which may be similar or identical to removable adhesive backer 528 of FIG. 5) may be concurrently removed from main body 640, while rigid skirt 648 remains attached to main body 640. In some embodiments, a safety tab 650 may be removed from applicator 600. While in place in main body 640, safety tab 650 may prevent inadvertent activation of applicator 600.

Figure 6E:
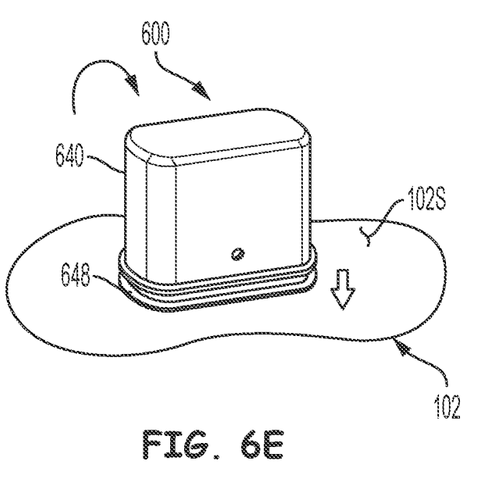

FIG. 6E shows applicator 600 turned upside down (from that shown in FIGS. 6A-D) and positioned onto a surface 102S of a user's skin 102 (a portion shown). More particularly, rigid skirt 648 is positioned on and engages the user's skin 102. Applicator 600 may then be actuated by pressing main body 640 towards the skin surface 102S. This action inserts the sensor of the sensor unit of CAM device 601 subcutaneously into the user's skin 102 similarly or identically as, e.g., sensor 112 of FIG. 1.

Figure 6F:
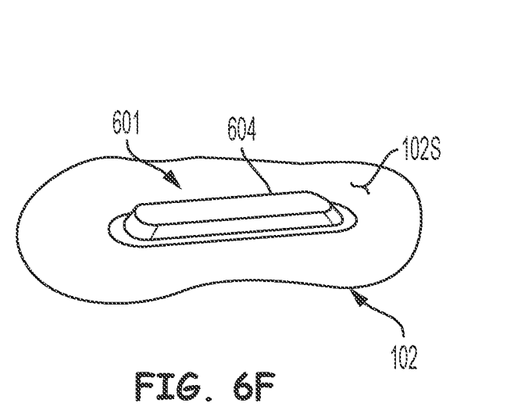

After actuation of applicator 600, applicator 600 (in particular, main body 640 and rigid skirt 648) may be removed, as shown in FIG. 6F, leaving behind CAM device 601 attached to a surface of the user's skin 102. CAM device 601 advantageously may have a soft and/or fabric cover 604, which may be similar or identical to cover 204 of FIG. 2. As shown, CAM device 601 advantageously also has a commonly shaped bandage-like appearance (see also FIG. 2) having (in plan view) two parallel long sides and two opposing bull-nosed (curved, radiused, and faceted) ends with an aspect ratio (AR) of length (L)-to-width (W) ranging from AR=2:1 to AR=4:1. Such an appearance may be less noticeable when attached to a user. The CAM device 601 may have a flesh colored appearance. The user may thus avoid having to explain what that "thing" is attached to their skin 102, which could be awkward or embarrassing to the user.

Figure 7:
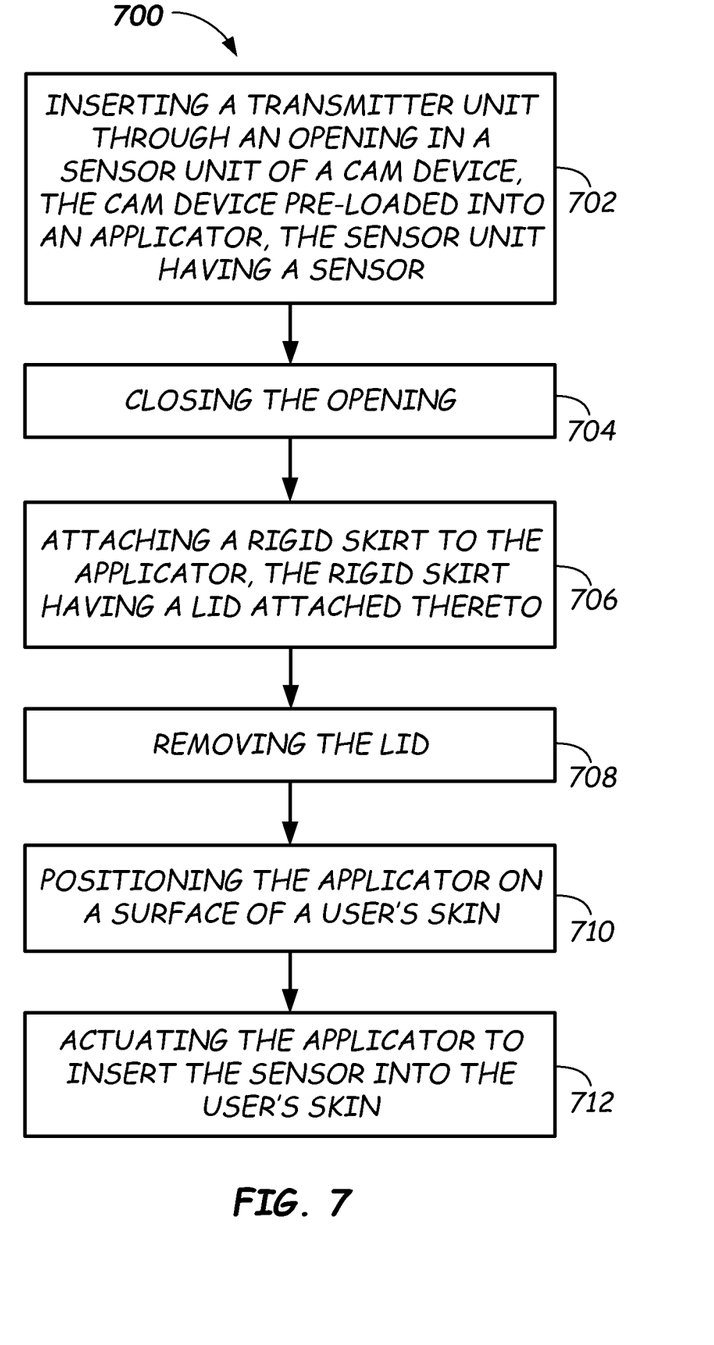
FIG. 7 illustrates a flowchart of a method of preparing and applying a CAM device to a user's skin according to embodiments provided herein.

FIG. 7 illustrates a method 700 of preparing and applying a CAM device (e.g., cam device 601) to a user's skin (e.g., user's skin 102) according to one or more embodiments. At process block 702, method 700 may begin by inserting a transmitter unit (e.g., a long-life reusable wireless transmitter unit 114, 414) through an opening (e.g., closeable opening 644) in a sensor unit (e.g., sensor unit 108) of a CAM device (e.g., cam device 601) that is pre-loaded into an applicator (e.g., applicator 600) for attaching the CAM device to skin 102 of a user. The sensor unit has a sensor extending from both the sensor unit and the CAM device, such as, e.g., sensor 112 of FIG. 1. The long-life reusable wireless transmitter unit may be, e.g., transmitter unit 414 shown in FIG. 6A being inserted through closeable opening 644 into a sensor unit of CAM device 601, which is pre-loaded into applicator 600.

Figure 8:
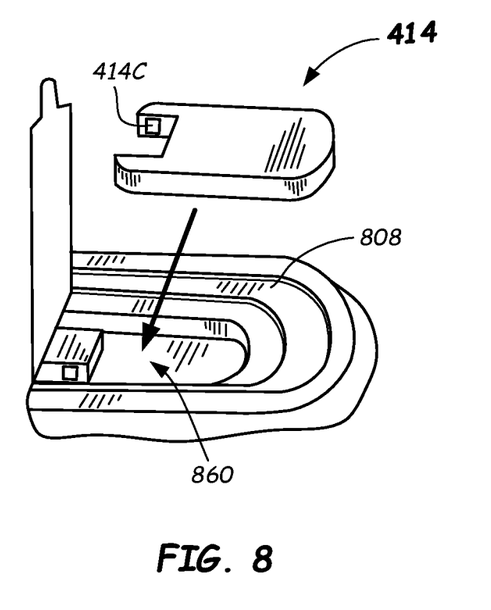
FIG. 8 illustrates a perspective view of a reusable transmitter unit and a bottom section of a sensor unit of a CAM device having an area form-fitted to receive the transmitter unit therein according to embodiments provided herein.

In some embodiments, the transmitter unit 114, 414 may be inserted into an area of the sensor unit 808 that is form-fitted and sized to receive the transmitter unit 114, 414. For example, FIG. 8 shows a bottom section of a sensor unit 808 having an area 860 form-fitted to receive transmitter unit 114, 414 according to one or more embodiments. Such a form-fitted area 860 may ensure that transmitter unit 114, 414, and in particular, electrical contacts 414C, are appropriately positioned and electrically connected within the sensor unit 808 to receive power and electrical signals from the sensor unit 808.

At process block 704, method 700 may include closing the closeable opening 644 after the transmitter unit 114, 414 has been inserted into the sensor unit 808. In some embodiments, the opening may be closed by a hinged flap, which is part of an adhesive assembly forming the bottom of the sensor unit and CAM device, as shown, e.g., by hinged adhesive flap 624 in FIG. 6B. In other embodiments, the closeable opening 644 may be closed in any suitable manner by any suitable structure.

At process block 706, method 700 may include attaching a rigid skirt to the applicator, wherein the rigid skirt has a lid attached thereto. For example, as shown in FIG. 6C, the rigid skirt may be rigid skirt 648 and the lid may be lid 646 coupled thereto.

At process block 708, method 700 may include removing the lid from the applicator, wherein the rigid skirt remains attached to the applicator. In some embodiments, e.g., removal of the lid 646 and safety key 650 results in the configuration of main body 640 and rigid skirt 648 of applicator 600 shown in FIG. 6D.

At process block 710, method 700 may include positioning the applicator on a surface 102S of the user's skin 102 (see, e.g., FIG. 6E). Suitable locations may include the user's abdomen or back of the upper arm.

At process block 712, method 700 may include actuating the applicator 600 to insert the sensor (e.g., sensor 112 (FIG. 1) into the user's skin 102. In some embodiments, the applicator 600 may be actuated by pressing the applicator 600 toward the user's skin 102, as indicated, e.g., in FIG. 6E. After actuation, the applicator 600 may be removed, leaving behind the CAM device 601 attached to a surface 102S of the user's skin 102.

In some embodiments, after expiration of the sensor 112, method 700 may further include process blocks (not shown) that include removing the CAM device 601 from the surface 102S of the user's skin 102, removing the transmitter unit 114, 414 from the sensor unit 108, 808 through the opening 644 (e.g., reversing the process shown in FIGS. 6A and 6B), and reusing the transmitter unit 114, 414 in another new sensor unit.

While this disclosure is susceptible to various modifications and alternative forms, specific method and apparatus embodiments have been shown by way of example in the drawings and are described in detail herein. It should be understood, however, that the particular methods and apparatus disclosed herein are not intended to limit the disclosure or the following claims.

What is claimed is:

1. A wearable continuous analyte monitoring (CAM) system, comprising:
 a CAM device comprising:
  a transmitter unit comprising an enclosure and wireless transmitter circuitry completely sealed within the enclosure, wherein the wireless transmitter circuitry is operative to receive and wirelessly transmit electrical signals indicative of an analyte level, and the transmitter unit has no power source therein and has electrical contacts on the enclosure for receiving power and the electrical signals;
  a sensor unit comprising a power source and a sensor, the sensor extending through the sensor unit and configured to be inserted into skin of a user, wherein the sensor unit has a closable opening for receiving the transmitter unit there through, the sensor unit configured to generate the electrical signals indicative of the analyte level and to electrically connect to the electrical contacts of the transmitter unit in response to receiving the transmitter unit through the closable opening,
  wherein the sensor unit is disposable, and the transmitter unit is removable from the sensor unit through the closable opening and is reusable in another sensor unit; and
  a CAM cover comprising a fabric covering the sensor unit; and
 an applicator comprising:
  a main body configured to receive the CAM device therein;
  a safety cover positioned over the sensor of the sensor unit received in the main body; and
  a rigid skirt attachable to the main body with the CAM device received in the main body, the rigid skirt comprising:
   a lid coupled thereto, the lid and the safety cover removable together after the rigid skirt is attached to the main body with the CAM device received in the main body.

2. The CAM system of claim 1, wherein the closable opening comprises a hinged flap.

3. The CAM system of claim 1, wherein the sensor unit further comprises an adhesive assembly that includes the closable opening, and the sensor extends through the adhesive assembly.

4. The CAM system of claim 3, wherein the sensor unit further comprises a flexible housing that forms an enclosure with the adhesive assembly.

5. The CAM system of claim 1, wherein the sensor unit has an area therein form-fitted to receive the transmitter unit therein.

6. The CAM system of claim 1, wherein the CAM device is a continuous glucose monitoring device.

7. The CAM system of claim 1, comprising a structure of the CAM device wherein L/H ratio>4, wherein L/H ratio is defined as a length-to-height ratio of length L divided by height H.

8. The CAM system of claim 7, comprising L/H ratio>6.

9. The CAM system of claim 7, comprising L/H ratio>8.

10. The CAM system of claim 1, comprising two parallel sides and two opposing curved ends with AR from 2:1 to 4:1, wherein AR is an aspect ratio of length (L) to width (W).

11. A CAM system, comprising:
 a CAM device comprising:
  a transmitter unit comprising an enclosure and wireless transmitter circuitry completely sealed within the enclosure, wherein the wireless transmitter circuitry is operative to receive and wirelessly transmit electrical signals indicative of an analyte level, and the transmitter unit has no power source therein and has electrical contacts on the enclosure for receiving power and the electrical signals;
  a sensor unit comprising a power source and a sensor, the sensor extending through the sensor unit and configured to be inserted into skin of a user, wherein the sensor unit has a closable opening for receiving the transmitter unit there through, the sensor unit configured to generate the electrical signals indicative of the analyte level and to electrically connect to the electrical contacts of the transmitter unit in response to receiving the transmitter unit through the closable opening,
  wherein the sensor unit is disposable, and the transmitter unit is removable from the sensor unit through the closable opening and is reusable in another sensor unit; and
  a CAM cover comprising a fabric covering the sensor unit; and
 an applicator having a main body configured to receive the CAM device therein, the applicator including a safety cover positioned over the sensor of the sensor unit received in the main body, the applicator further including a rigid skirt attachable to the main body with the CAM device received in the main body,
 wherein the rigid skirt includes a lid coupled thereto, the lid and the safety cover removable together after the rigid skirt is attached to the main body with the CAM device received in the main body.

12. The CAM system of claim 11, wherein the lid is attachable to the safety cover of the applicator.

13. A method of preparing and applying a continuous analyte monitoring (CAM) device to a user's skin, the method comprising:
 inserting a transmitter unit through an opening in a sensor unit of the CAM device, the CAM device pre-loaded into an applicator,
  wherein the transmitter unit comprises an enclosure and a wireless transmitter circuitry completely sealed within the enclosure, wherein the wireless transmitter circuitry is operative to receive and wirelessly transmit electrical signals indicative of an analyte level, and the transmitter unit has no power source therein and has electrical contacts on the enclosure for receiving power and the electrical signals,
  wherein the sensor unit comprises a power source and a sensor, the sensor extending through the sensor unit and the CAM device and configured to be inserted into skin of a user, wherein the sensor unit has a closable opening for receiving the transmitter unit there through, the sensor unit configured to generate the electrical signals indicative of the analyte level and to electrically connect to the electrical contacts of the transmitter unit in response to receiving the transmitter unit through the closable opening,
  wherein the sensor unit is disposable, and the transmitter unit is removable from the sensor unit through the closable opening and is reusable in another sensor unit,
  wherein the CAM device comprises a CAM cover comprising a fabric covering the sensor unit, and
  wherein the applicator comprises:
   a main body configured to receive the CAM device therein;
   a safety cover positioned over the sensor of the sensor unit received in the main body; and
   a rigid skirt attachable to the main body with the CAM device receivable in the main body, the rigid skirt comprising:
    a lid coupled thereto, the lid and the safety cover removable together after the rigid skirt is attached to the main body with the CAM device received in the main body;
 closing the opening;
 attaching the rigid skirt to the applicator;
 removing the lid;
 positioning the applicator on a surface of the user's skin; and
 actuating the applicator to insert the sensor into the user's skin.

14. The method of claim 13 wherein the inserting the transmitter unit comprises inserting the transmitter unit through the opening in the sensor unit of the CAM device into an area of the sensor unit form-fitted to receive the transmitter unit.

15. The method of claim 13 wherein the closing of the opening comprises sealing a hinged flap of the CAM device over the opening.

16. The method of claim 15, wherein the closing of the opening further comprises removing an adhesive flap backer from the hinged flap prior to the sealing the hinged flap.

17. The method of claim 13, wherein the removing the lid comprises removing the lid and an adhesive backer from the CAM device.

18. The method of claim 13 wherein the removing the lid comprises removing the lid and the safety cover positioned over the sensor.

19. The method of claim 13 wherein the actuating the applicator further comprises attaching the CAM device to the surface of the user's skin.

20. The method of claim 13, further comprising:
 removing the CAM device from the surface of the user's skin; and
 removing the transmitter unit from the sensor unit through the opening.

21. The method of claim 20 further comprising reusing the transmitter unit in another sensor unit.

22. The method of claim 13 wherein the CAM device is a continuous glucose monitoring device.

\* \* \* \* \*